United States Patent [19]

von Schmeling et al.

[11] 4,044,139
[45] Aug. 23, 1977

[54] BIS(DIPHENYLAMINOMETHANE) ANTIMICROBIAL AGENTS

[75] Inventors: Bogislav von Schmeling, Hamden, Conn.; Walter R. Boos, Guelph, Canada

[73] Assignees: Uniroyal, Inc., New York, N.Y.; Uniroyal Ltd., Canada

[21] Appl. No.: 658,004

[22] Filed: Feb. 13, 1976

Related U.S. Application Data

[62] Division of Ser. No. 440,941, Feb. 8, 1974, Pat. No. 3,954,868, which is a division of Ser. No. 231,385, March 2, 1972, Pat. No. 3,808,316.

[51] Int. Cl.$^2$ .................. A61K 31/44; C07D 213/36
[52] U.S. Cl. ................... 424/263; 424/278; 424/316; 424/330; 252/8.8; 252/107; 260/296 R; 260/346.71; 260/501 J; 260/562 P; 260/566 A; 260/570 R; 260/591
[58] Field of Search ........ 260/296 R, 570 R, 570.5 P, 260/346.2 M; 424/263, 330, 278

[56] References Cited

U.S. PATENT DOCUMENTS

| | | | |
|---|---|---|---|
| 3,128,280 | 4/1964 | Rorig | 260/295 |
| 3,663,712 | 5/1972 | von Schmeling et al. | 424/330 |
| 3,808,316 | 4/1974 | von Schmeling et al. | 424/330 |
| 3,954,868 | 4/1976 | von Schmeling et al. | 260/346.2 MX |

OTHER PUBLICATIONS

LaForge, J. Am. Chem. Soc., vol. 50, pp. 2484 to 2487 (1928).
Matveev et al., Chem. Abstracts, vol. 55, cols. 6433-6434 (1961).
Burger, Medicinal Chemistry, 2nd ed., frontispage and pp. 78-79, Interscience Publishers Inc. NY (1960).
Chemical Abstracts, Sixth Collective Index, p. 12528s (1966).
Klingsberg, Pyridine and Its Derivatives, Part Three, frontispage and p. 134, Interscience Publishers, NY (1962).

*Primary Examiner*—John D. Randolph
*Attorney, Agent, or Firm*—James J. Long

[57] ABSTRACT

New chemicals containing two diphenylaminomethane groups, linked together by a moiety other than oxygen, e.g., 1,2-bis[4-(3-methyl-alpha-aminobenzyl)phenoxy]ethane, are effective antimicrobial agents useful as agricultural or industrial fungicides and bactericides.

10 Claims, No Drawings

BIS(DIPHENYLAMINOMETHANE) ANTIMICROBIAL AGENTS

This application is a division of our copending application Ser. No. 440,941, filed Feb. 8, 1974 (now U.S. Pat. No. 3,954,868, issued May 4, 1976), which is in turn a division of our application Ser. No. 231,385, filed Mar. 2, 1972 (now U.S. Pat. No. 3,808,316, issued Apr. 30, 1974).

This invention relates to new chemicals which contain two diphenylaminomethyl groups linked together by a moiety other than oxygen, and to a method of controlling microorganisms with such chemicals.

In our copending application Ser. No. 861,153, filed Sept. 25, 1969, now U.S. Pat. No. 3,663,172, issued May 16, 1972, control of microorganisms with 4,4'-bis(alpha-aminobenzyl) diphenyl ethers is disclosed.

The present invention is directed to chemicals which are bisdiphenylaminomethanes, wherein two diphenylaminomethane groups are linked together by a moiety other than oxygen or have a phenyl or other cyclic radical in common, as represented for example by chemicals of the following formulas I or II:

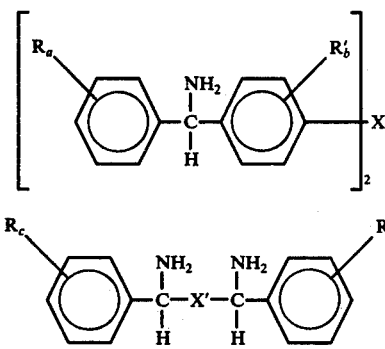

I

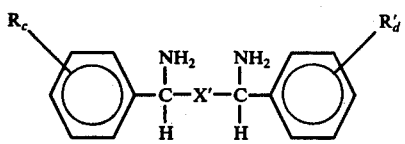

II wherein X represents a connecting moiety selected for instance from the group consisting of —O(CH$_2$)$_n$O— (wherein $n$ is, e.g., 2 to 4).

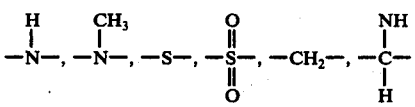

and furyl fused to one phenyl group of each diphenylaminomethane moiety, X' represents phenylene or pyridinediyl, R and R' are the same or different and are hydrogen or various substituents such as hydrocarbyl (e.g., alkyl, preferably lower alkyl as in methyl) or non-hydrocarbyl (e.g., alkoxy, preferably lower alkoxy as in methoxy, or aryloxy as in phenoxy, etc.), and a, b, c and d are usually 1 or 2 (preferably 1).

Thus, exemplary chemicals are those in which the linking group is —O(CH$_2$)$_n$O— as in the structures:

Chemical A

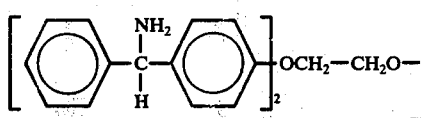

Chemical B

-continued

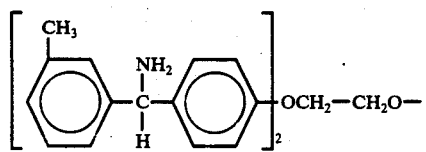

Chemical C

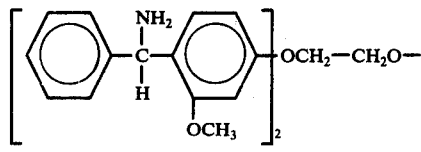

Chemical D

Chemical E

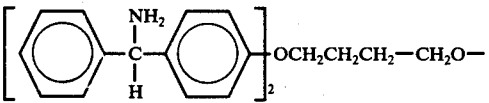

or amino (e.g., —NH—, —NCH$_3$—, etc.) as in the structures:

Chemical F

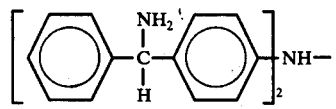

Chemical G

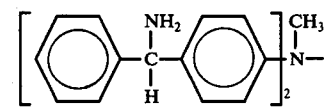

or —S— or —SO$_2$— as in the structures:

Chemical H

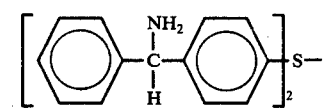

Chemical I

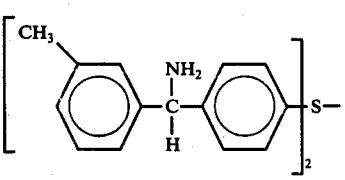

Chemical J

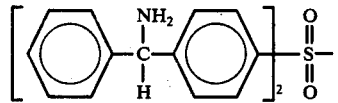

or —CH$_2$— or —CHNH$_2$— as in the structures:

Chemical K

-continued

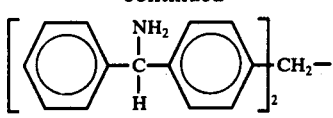

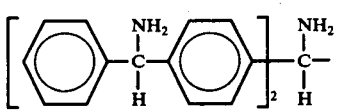

Chemical L or phenyl group as in the structures:

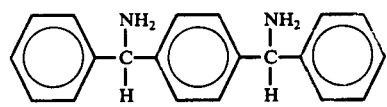

Chemical M

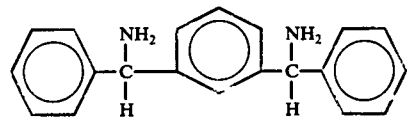

Chemical N

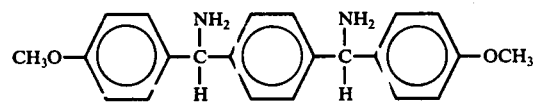

Chemical O

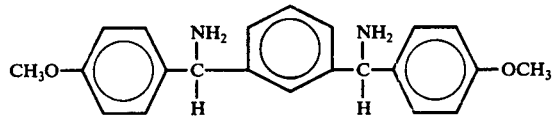

Chemical P

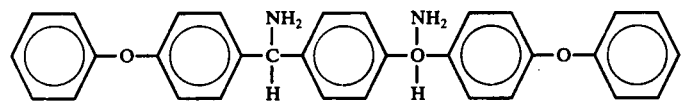

Chemical Q or heterocyclic ring as in the structures:

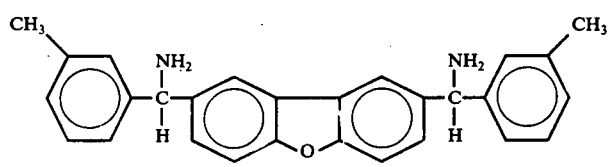

Chemical R

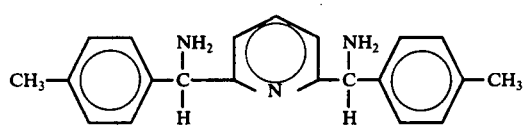

Chemical S

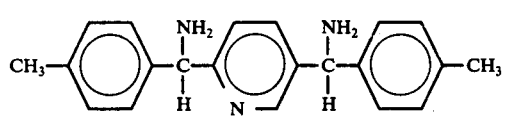

Chemical T

Preferred chemicals are 1,2-bis[4-(3-methyl-alpha-aminobenzyl)phenoxy]ethane (Chemical B), 1,3-bis[4-(alpha-aminobenzyl)phenoxy]propane (Chemical D), 1,4-bis[4-(alpha-aminobenzyl)phenoxy]butane (Chemical E), 4,4'-thiobis(alpha-phenylbenzylamine) (Chemical H), and 4,4'-bis(alpha-amino-alpha-phenyltolyl)methane (Chemical K).

In one aspect the invention involves applying to a locus, subject to attack by microorganisms, a chemical of the kind described.

The invention makes possible the control, in vivo or in vitro, of such microorganisms as bacteria or fungi, whether in agricultural uses, or non-agricultural uses such as the protection of fuel oil, fabrics, etc., from injury by microorganisms. Agricultural uses include the control of vegetable and fruit diseases such as the bacterial blights and leaf spots.

One method of preparing chemicals of the invention is represented by the equations:

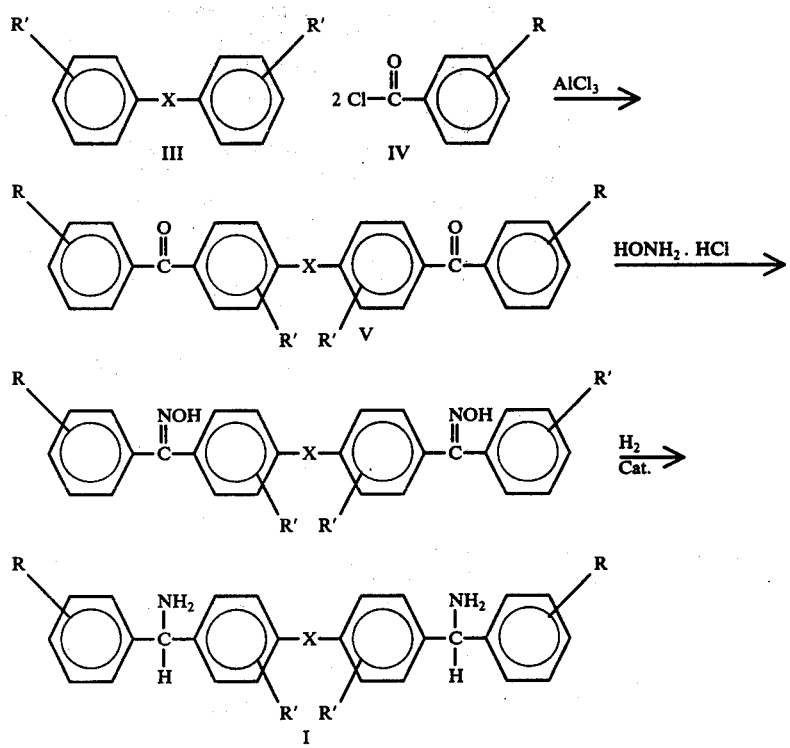

In this method, hereinafter called Method 1, an appropriate starting compound III having two phenyl groups linked together by a moiety other than oxygen is subjected to a Friedel-Crafts reaction with an aromatic acid chloride IV to form a diketone V. The diketone V may be converted, by reaction with hydroxylamine hydrochloride, into the corresponding dioxime VI, which may in turn be converted into the desired diamine I by catalytic hydrogenation.

A second method of preparing chemicals of the invention, hereinafter referred to as Method 2, is represented by the equations:

In method 2, an aromatic diketone V is converted by a Leuckart reaction, into the corresponding bisformamide VII, which may in turn be hydrolyzed to the desired amine I by acid hydrolysis followed by treatment with a base.

A third method of preparation (Method 3) is represented by the equations:

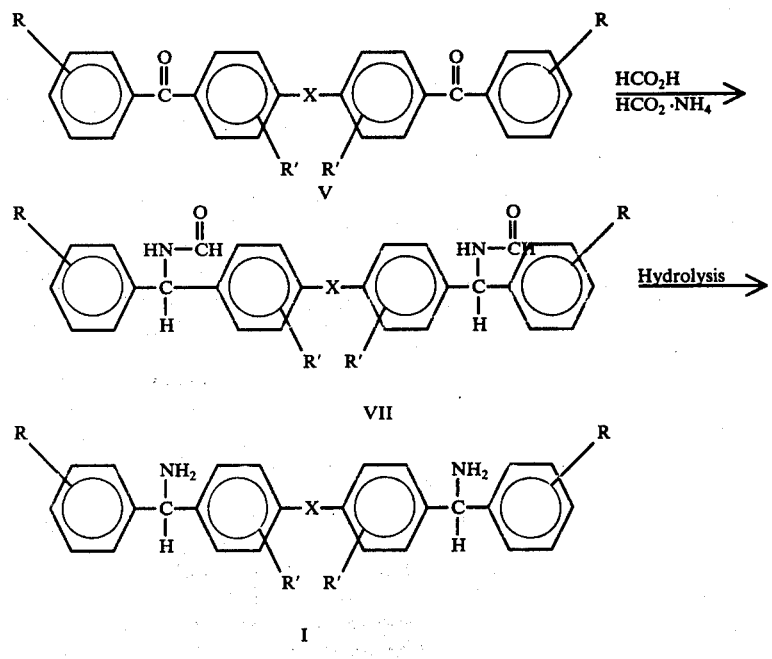

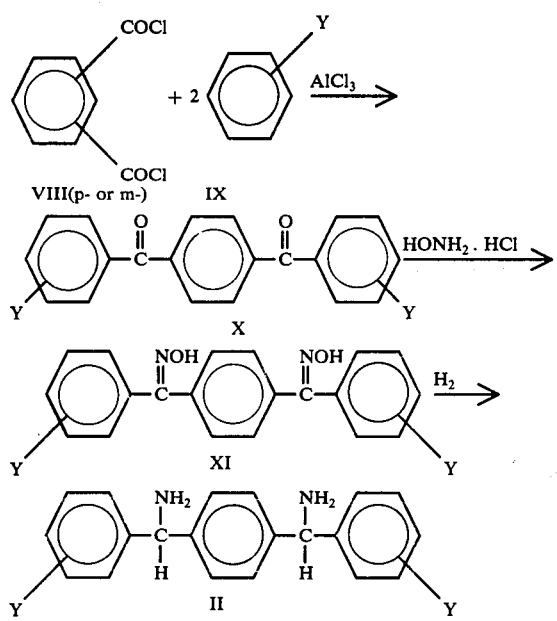

In Method 3 an appropriate aromatic diacid dichloride VIII is converted by a Friedel-Crafts reaction with an appropriate aromatic compound IX, to a diketone X. The diketone X in turn may be converted by reaction with hydroxylamine hydrochloride to the corresponding dioxime XI, which may be reduced to the desired diamine II by catalytic hydrogenation.

It can be seen from the structures of the diamines I and II that they have two centers of asymmetry and that compounds prepared by the above methods are a mixture of several stereoisomers. These are not readily separable by crystallization or otherwise.

The chemicals employed in this invention possess a high degree of bactericidal activity controlling such bacteria as *Pseudomonas aeruginosa* (Schroeter) Migula, *Escherichia coli* (Migula) Castellani and Chalmers, *Staphylococcus aureus* Rosenbach, *Desulfovibrio desulfuricans* (Beijerinck) Kluyver and van Niel, *Streptococcus pyogenes* Rosenbach, *Xanthomonas phaseoli* (Smith) Dowson and *Erwinia amylovora* (Burrill) Winslow et al.

The chemicals employed in this invention also control fungi such as *Alternaria solani* (Ellis and Mastin) Sorauer, *Claeosporium resinae* f. *resinae* de Vries, *Hormodendrum* spp., *Chaetomium globosum* Kunze ex Fries, *Aurobasidum* (Pullularia)*pullulans* (de Bary and Lowe) Berkhout, *Candida albicans* (Robin) Berkhout, *Trichophyton mentagrophytes* (Robin) Blanchard and *Uromyces phaseoli typica* Arth.

In agricultural applications, the chemical may be applied directly to the plants (e.g., seeds, foliage) or to soil in which plant life is growing or is to be grown, to protect the plant life against the harmful effects of such pathogenic microorganisms as bacteria and fungi. For example, the chemical may be applied to seeds by tumbling the chemical with the seeds, either alone or in admixture with a powdered solid carrier, to coat the seeds. Typical powdered solid carriers are the various mineral silicates, e.g., mica, talc, pyrophyllite, and clays. The chemical may also be applied to the seeds in admixture with conventional surface-active wetting agents, with or without additional powdered solid carrier, as by first wetting the mixture with a small amount of water and then tumbling the seeds in the slurry. The surface-active wetting agents that may be used with the chemical may be any of the conventional anionic, nonionic, or cationic surface-active agents. Such surface-active agents are well known and reference is made to U.S. Pat. No. 2,547,724, columns 3 and 4, for detailed examples of the same. As a seed protectant, the amount of the chemical coated on the seeds will be ¼ to 12 ounces per hundred pounds of the seed. As a soil treatment for fungi and the like, the chemical may be applied as a dust in admixture with sand or soil or a powdered solid carrier such as a mineral silicate, with or without an additional surface-active wetting agent, to the furrows with the planting of the seeds, or the chemical may be applied as an aqueous spray, if desired including a surface-active dispersing agent, or a surface-active dispersing agent and a powdered solid carrier, to the seed rows before, or with, or after planting the seeds. As a soil treatment, the amount of the chemical applied to the seed rows will be from 0.1 to 10 pounds per acre applied to the seed rows based on rows 2 inches wide and 2 inches deep a distance of 40 inches apart. Also, as a soil treatment, the chemical may be applied broadcast as a similar dust or aqueous spray with an application rate of 1.0 to 100 pounds per acre. As a foliage treatment (e.g., fungicidal or bactericidal), the chemical may be applied to growing plants at a rate of ¼ to 10 pounds per acre. Such application is generally as an aqueous spray which also contains a surface-active dispersing agent, with or without a powdered solid carrier or hydrocarbon solvent. These sprays usually are repeated at time intervals ranging from three days to two weeks during the growing season. Typical formulations are as follows:

a) Emulsifiable concentrate:
   48.1%  Bis(diphenylaminomethane) chemical
   11.1%  Surfactant (e.g., Tween [trademark] 80;
          polyoxyethylene sorbitan monooleate)
   40.8%  Xylene
   100.0% Total b) Wettable powder:
   75.0%  Bis(diphenylaminomethane) chemical
   2.0%   Triton (trademark) X-120
   2.0%   Daxad (trademark) -11
   21.0%  Dixie clay
   100.0% Total Triton X-120 is an alkylaryl polyether alcohol (9–10 moles polyethylene oxide) in dry powdered form (40% active on an insoluble carrier). The active ingredient in Triton X-120 is Triton X-100, which is a liquid nonionic surfactant (isooctylphenylpolyethoxyethanol, obtained by condensing the alkylphenylphenol with ethylene oxide). Daxad-11 is polymerized sodium salt of alkylnaphthalene sulfonic acid (more particularly, the sodium salts of dinaphthylmethane sulfonic acids obtained from naphthalene, sulfuric acid and formaldehyde, according to U.S. Pat. No. 1,336,759, Schmidt, Apr. 13, 1920).

As industrial bactericides and fungicides, the present chemicals may be used to control bacteria or fungi by contacting the bacteria or fungi with the chemical in any suitable manner. Materials capable of nourishing bacteria and fungi may be protected from destruction by such pests by contacting, mixing, or impregnating with the chemical. Such materials include petroleum oils, fuel oils, fabrics, cellulosic materials in various forms including textiles, wood, paper, etc. In order to broaden their spectrum or increase their effect the chemicals may be combined with other pesticidal control agents such as fungicides, bactericides, insecticides or miticides.

Chemicals of this invention may be used as antimicrobial agents for the preservation of petroleum hydrocarbons. Petroleum hydrocarbons are known to be utilized by bacteria and fungi as a food source. The resulting increase in microbial population can cause various problems such as filter plugging, metal corrosion of storage tanks and aircraft fuel tanks, fuel line plugging and flame-outs. A biocide added to hydrocarbon fuels can prevent microbial growth and eliminate the problems mentioned.

Chemicals of this invention may be used as material preservatives against cellulose-degrading fungi causing deterioration of textiles, paper, wood, etc.

The chemicals of the invention may be incorporated in soap to be used in combatting bacteria and fungi.

Equivalent to the chemicals per se in many cases are the salts thereof (e.g., hydrochlorides, acetates, citrates), which are readily provided by treatment with an appropriate acid.

The following examples, in which all quantities are expressed by weight unless otherwise indicated, will serve to illustrate the practice of the invention in more detail.

EXAMPLE 1

This Example uses Method 1 to prepare Chemical B, 1,2-bis[4-(3-methyl-alpha-aminobenzyl)phenoxy]ethane.

Step 1. Preparation of 1,2-bis[4-(3-methylbenzoyl)-phenoxy]ethane.

To a stirred suspension of anhydrous aluminum chloride (24 g) in 300 ml dry 1,2-dichloroethane is added 1,2-diphenoxyethane (17.8 g, 0.083 mole) at room temperature. To this mixture is added over a period of 30 minutes m-toluoyl chloride (27 g, 0.17 mole). The temperature of the reaction rises to 40° (all temperatures are Centigrade) and hydrogen chloride gas evolves from the mixture. Following the addition of the m-toluoyl chloride the reaction is externally heated to 65° plus or minus 3°. This temperature and stirring are maintained for 22 hours. The mixture is then allowed to cool to room temperature and poured on 1 kg of crushed ice to destroy the aluminum chloride complex. The ice is allowed to melt and the water separates from the organic layer. The latter is washed twice with 200 ml of 10% hydrochloric acid, three times with water and the solvent removed by distillation. The residual crude crystals are crystallized from dichloroethane, yield 15.9 g (43%) mp 164° – 167°. Calculated for $C_{30}H_{26}O_4$: C, 79.98%; H, 5.82%. Found: C, 79.65%; H, 5.88%.

Step 2. Preparation of 1,2-bis[4-(3-methylbenzoyl)-phenoxy]ethane dioxime.

A mixture of 1,2-bis[4-(3-methylbenzoyl)phenoxy]ethane (13.5 g, 0.03 mole), hydroxylamine hydrochloride (8.3 g, 0.1 mole), hydrated sodium acetate (18 g, 0.13 mole) and 300 ml ethyl alcohol is heated to gentle reflux for 24 hours, then added to 1.5 l water and allowed to stand for 18 hours. The resulting crystals are filtered, washed with water, dried first at room temperature then in an oven at 90° for 5 hours. The yield of the oxime is 12.3 g (85% of theory) mp 151°–153°. Calculated for $C_{30}H_{28}N_2O_4$: C, 74.98%; H, 5.87%; N, 5.83%. Found: C, 74.75%; H, 6.01%; N, 5.36%.

Step 3. Preparation of 1,2-bis[4-(3-methyl-alpha-aminobenzyl)phenoxy]ethane.

A reaction mixture is prepared from 1,2-bis[4-(3-methylbenzoyl)phenoxy]ethane dioxime (10.6 g, 0.022 mole), 400 ml absolute ethyl alcohol saturated with ammonia gas and Raney nickel catalyst W-6 (2 g). This mixture is subjected to 500 psi hydrogen pressure, heated to 90° and stirred for seven hours. The Raney nickel is removed by filtration and the alcohol and ammonia by distillation. The residual crude material is crystallized from ethanol to yield 4.2 g (42%) of material mp 113°–115°.

Calculated for $C_{30}H_{32}N_2O_2$: C, 79.61%; H, 7.13%; N, 6.19%.

Found: C, 79.36%; H, 7.27%; N, 5.80%.

The infrared spectrum of the product indicates absence of ketone groups (i.e., the intermediate) and the presence of amine groups.

EXAMPLE 2

This Example illustrates the preparation of Chemical E, 1,4-bis[4-(alpha-aminobenzyl)phenoxy]butane, by Method 1, from 1,4-diphenoxy-n-butane and benzoyl chloride. The procedure of Example 1 is followed.

Step 1: 1,4-Bis(4-benzoylphenoxy)butane.

1,4-Diphenoxy-n-butane (24.2 g) and benzoyl chloride (29 g) are reacted in 250 ml of 1,2-dichloroethane in the presence of aluminum chloride (28 g) for 4 hours at 60° to yield 18.3 g (41% of theory) of colorless crystals mp 163°–164°. Calculated for $C_{30}H_{26}O_4$: C, 79.98% H, 5.82%. Found: C, 80.16%; H, 5.98%.

Step 2. 1,4-Bis(4-benzoylphenoxy)butane dioxime.

The diketone from Step 1 (13.5 g), hydroxylamine hydrochloride (7 g) and sodium acetate (15 g) are refluxed in a mixture of ethyl alcohol (250 ml) and dioxane (125 ml) for 16 hours to yield 6.3 g (44% of theory) of colorless crystals mp 154°–156°.

Step 3. 1,4-Bis[4-(alpha-aminobenzyl)phenoxy]butane (E).

The dioxime from Step 2 (6.3 g) is dissolved in ethyl alcohol saturated with ammonia gas (220 ml) and Raney nickel W-6 (2.3 g) added. The mixture is subjected to 650 psi hydrogen pressure and heated to 90° for twenty-two hours. The catalyst is removed by filtration and the solvent is removed by distillation to yield 4.1 g (69% of theory) of colorless crystals mp 120°–123°.

Calculated for $C_{30}H_{32}N_2O_2$: C, 79.61%; H, 7.13%; N, 6.19%. Found: C, 79.47%; H, 7.35% N, 6.79%.

EXAMPLE 3

Using Method 1, Chemical D, 1,3-bis[4-(alpha-aminobenzyl) phenoxy]propane, is prepared from 1,3-diphenoxy-n-propane and benzoyl chloride following the procedure of Example 1.

Step 1: 1,3-Bis(4-benzoylphenoxy)propane.

1,3-Diphenoxypropane (22.8 g), benzoyl chloride (31 g) and anhydrous aluminum chloride (33 g) are reacted in 1,2-dichloroethane (300 ml) for eighteen hours at 70° to yield 33.4 g (77% of theory) of colorless crystals mp 146°–148°.

Step 2: 1,3-Bis(4-benzoylphenoxy)propane dioxime.

The diketone from Step 1 (26.2 g), hydroxylamine hydrochloride, (16.7 g) and sodium acetate (36 g) are refluxed in a mixture of 350 ml of ethyl alcohol and 350 ml of dioxane for 25 hours to yield 27.5 g (98% of theory) of colorless crystals mp 205°–208°.

Step 3: 1,3-Bis[4-(alpha-aminobenzyl)phenoxy]propane (D).

The dioxime from Step 2 (20 g) is dissolved in ethyl alcohol saturated with ammonia gas (220 ml) and Raney nickel W-6 (2 g) added. The mixture is subjected to 500 psi hydrogen pressure and heated at 90° for four hours. The catalyst is removed by filtration and the solvent is removed by distillation to yield 15.5 g (83% of theory) of pale yellow crystals mp 118°–119°. Calculated for $C_{29}H_{30}N_2O_2$: C, 79.42%; H, 6.90%; N, 6.39%. Found: C, 79.14% H, 6.57%; N, 6.89%.

EXAMPLE 4

Using Method 1, Chemical A, 1,2-bis[4-(alpha-aminobenzyl)phenoxy]ethane, is prepard by the procedure of Example 1, starting with 1,2-diphenoxyethane and benzoyl chloride; mp 116°–120°. Calculated for $C_{28}H_{28}N_2O_2$: C, 79.21%; H, 6.65%; N, 6.60%. Found: C, 79.29%; H, 6.52%; N, 6.39%.

EXAMPLE 5

Using Method 1, and following the procedure of Example 1, Chemical K, 4,4'-bis(alpha-amino-alpha-phenyltolyl)methane, is prepared from diphenylmethane and benzoyl chloride.

Step 1: 4,4'-Dibenzyldiphenylmethane.

(Preparation of this chemical is reported by G. Wittig et al. Ber. 61, 858 (1928). Diphenylmethane (84 g) and benzoyl chloride (147 g) are reacted in the presence of aluminum chloride (147.5 g) in 1,2-dichloroethane (400 ml) for eighteen hours at 20°. Yield 22 g (12% of theory) of yellow crystals mp 141°—144°.

Step 2: 4,4'-Dibenzoyldiphenylmethane dioxime.

The diketone from Step 1 (16 g) hydroxylamine hydrochloride (7 g), and sodium acetate (14 g) are refluxed in ethyl alcohol (300 ml) for eleven hours. The reaction mixture is added to 1 l of water yielding 17 g (98% of theory) pale yellow crystals mp 210°–212°.

Step 3: 4,4'-Bis(alpha-amino-alpha-phenyltolyl)methane (K).

The dioxime from Step 2 (17 g) is dissolved in ethyl alcohol (225 ml) saturated with ammonia gas and Raney nickel W-6 (2.3 g) added. The mixture is subjected to 650 psi hydrogen pressure and heated at 100° for 6 hours. The catalyst is removed by filtration and 175 ml of solvent by distillation. The yellow-brown precipitate is filtered and dried. Yield 13 g (82% of theory) mp 94°–98°. Calculated for $C_{27}H_{26}N_2$: C, 85.67%; H, 6.92%; N, 7.40%. Found: C, 85.60%; H, 6.82%; N, 6.91%.

EXAMPLE 6

1,2-Bis[4-(alpha-aminobenzyl)-3-methoxyphenoxy]ethane, Chemical C, is prepared from 1,2-bis(3-methoxyphenoxy)ethane and benzoyl chloride, using the procedure of Example 1, Method 1. The structure is confirmed by infrared analysis, which indicates absence of ketone groups (i.e., intermediate) and presence of amine groups (product).

EXAMPLE 7

4,4'-Bis(alpha-aminobenzylamine, Chemical F, is prepared from diphenylamine and benzoyl chloride, using the procedure of Example 1, Method 1. The structure is confirmed by infrared analysis, which indicates absence of ketone groups (i.e., intermediate) and presence of amine groups (product).

EXAMPLE 8

4,4'-Bis(alpha-aminobenzyl)N-methyldiphenylamine, Chemical G, is prepared from diphenylmethylamine, and benzoyl chloride, using the procedure of Example 1, Method 1. The diamine dihydrochloride melts at 202°–210°; its structure is confirmed by infrared analysis which indicates absence of ketone groups (i.e., intermediate) and presence of amine groups (product).

EXAMPLE 9

4,4'-Thiobis[alpha-(3-methylphenyl)benzylamine], Chemical I, is prepared from diphenyl sulfide and m-toluoyl chloride, using the procedure of Example 1, Method 1. The structure is confirmed by infrared analysis which indicates absence of ketone groups (i.e., intermediate) and presence of amine groups (product).

EXAMPLE 10

1,1-Bis(alpha-amino-alpha-phenyl-p-tolyl)methylamine, Chemical L, is prepared as follows:

Step 1: 4,4'-Dibenzoylbenzophenone is prepared by oxidation of 4,4'-dibenzoyldiphenylmethane (Chemical K, Step 1, 4.4 g) with chromium trioxide (4.7 g) by refluxing for four hours in 100 ml glacial acetic acid. Acetic acid is removed by distillation and the crude product recrystallized from ethyl alcohol, yield 2.9 g (65% of theory) mp 224°–228° [Reported by E. Connerade, Bull. soc. chim. Belg. 44. 411–24 (1935)].

Step 2: 4,4'-Dibenzoylbenzophenone trioxime. The triketone from Step I (2.9 g), hydroxylamine hydrochloride (3.1 g), and sodium acetate (3.6 g) are suspended in n-butyl alcohol (125 ml) and refluxed for 23 hours. The butyl alcohol is removed by distillation and the crude crystals are suspended in ethyl alcohol (100 ml) and added to 600 ml of water. A colorless crystalline material is collected by filtration and dried to yield 3 g (93% of theory) mp 224°–225°.

Step 3: 1,1-Bis(alpha-amino-alpha-phenyl-p-tolyl)methylamine (L). The trioxime from Step 2 (3 g) is dissolved in ethyl alcohol (250 ml) saturated with ammonia gas and Raney nickel W-6 (2 g) added. The mixture is subjected to 500 psi hydrogen pressure and heated to 90° for 2 hours. The catalyst is removed by filtration and 220 ml ethyl alcohol by distillation. A pale yellow crystalline material is filtered and dried. Yield 2.5 g (92% of theory) mp 182–185°. Calculated for $C_{27}H_{27}n_3$: C, 82.4%; H, 6.92%; N, 10.68%. Found: C, 82.41%; H, 6.95%; N, 10.70%.

EXAMPLE 11

Chemical R, 2,8-bis(3-methyl-alpha-aminobenzyl)-dibenzofuran, is prepared by Method 2, as follows:

Step 1: 2,8-Bis(3-methylbenzoyl)dibenzofuran is prepared according to the procedure of Step 1, Example 1. Dibenzofuran(42 g, 0.25 mole), m-toluoyl chloride (82 g, 0.53 mole), and anhydrous aluminum chloride (73 g, 0.55 mole) are reacted in carbon disulfide (250 ml) for 24 hours at 20°. The desired compound is obtained after recrystallization of the crude product from toluene, yield 22 g (23% of theory), mp 180°–181°. Calculated for $C_{28}H_{20}O_3$: C, 83.15%; H, 4.98%. Found: C, 83.21%; H, 5.08%.

Step 2:
2,8-Bis[alpha-(N-formyl)amino-3-methylbenzyl]-dibenzofuran.

The above diketone (16 g) together with formamide (40 g) and 90% formic acid (12 g) are heated for 20 hours at 170°. By this time a colorless precipitate has formed which is not isolated, but subjected directly to acid hydrolysis as described in Step 3.

Step 3:
2,8-Bis(alpha-amino-3-methylbenzyl)dibenzofuran(R).

The reaction product of Step 2 is added to 150 ml ethyl alcohol plus 20 ml water and 30 ml of hydrochloric acid (37%). The mixture is heated to 80° for two hours by which time a clear solution of the diamine hydrochloride is obtained. The ethyl alcohol is removed by distillation, 200 ml water added followed by sufficient solid sodium hydroxide to render the solution basic. The diamine is isolated by extraction with benzene, yield 11 g (69% of theory) of an amber material of high viscosity. This is identified as the dihydrochloride of (R) mp 293°–300°. Calculated for $C_{28}H_{28}Cl_2N_2O$: C, 70.15%; H, 5.85%; N, 5.85%. Found:
, 69.94%; H, 5.96% N, 5.94%.

EXAMPLE 12

Chemical H, 4,4'-thiobis(alpha-phenylbenzylamine), is prepared by Method 2.

Step 1: 4,4'-Thiobis(benzophenone) is prepared in a similar manner to Step 1, Example 1, essentially as reported by Dilthey et al., J. prakt. Chem. 124, 114 (1930). Diphenyl sulfide (85 g), benzoyl chloride (134 g) and aluminum chloride (134 g) were heated in 400 ml. of dichloroethane at 65° for 3 hours. Yield 122 g (68% theory) yellow crystals mp 183°–184°. Calculated for $C_{26}H_{18}O_2S$: C, 79.17% H, 4.5%. Found: C, 79.38; H, 4.91%.

Step 2: 4,4'-Thiobis[alpha-phenylbenzylamine(N-formyl)] is prepared in much the same way as was Chemical R, Step 2, Example 11. Diketone (5 g) from Step 1, formamide (30 g), and 90% formic acid (4 g) are heated at 170° for 16 hours. The resulting compound is not isolated but subjected directly to acid hydrolysis as described in Step 3.

Step 3: 4,4'-Thiobis(alpha-phenylbenzylamine) (H).

The reaction product of Step 2 is added to 100 ml water causing separation into two layers. The organic layer is extracted with chloroform which is removed by distillation. To the residue is added 20 ml ethyl alcohol, 5 ml 37% hydrochloric acid and 5 ml water. The mixture is heated at 80° for three hours. After cooling, enough acetone is added to the mixture to cause the diamine dihydrochloride to precipitate. This is filtered and dried, yield 5.7 g (92% of theory) colorless crystals mp 291°–294°. Calculated for $C_{26}H_{26}Cl_2N_2S$: C, 66.51%; H, 5.58%; N, 5.96%. Found: C, 66.19%; H, 5.76%; N, 5.70%.

This dihydrochloride can be converted to the corresponding diamine by treatment with a base.

EXAMPLE 13

4,4'-Bis(alpha-amino-alpha-phenyltolyl) sulfone, Chemical J, is prepared as follows:

The diketone prepared in Example 12, Step 1, (4,4' thiobis(benzophenone), 5 g) is dissolved in glacial acetic acid (300 ml), 32% hydrogen peroxide (3.2 ml) added and the mixture heated for 5 hours at 90°. The precipitate formed on the addition of the reaction mixture to water ( 2 l) is filtered and dried, yield 5.2 g (96% of theory) 4,4'-bis(benzophenone) sulfone mp 196°–197°.

The structure of the final product, Chemical J, obtained from this sulfone by the procedure of Method 1, is confirmed by infrared analysis which indicates the absence of ketone groups (i.e., intermediate) and presence of amine groups (product).

EXAMPLE 14

Using Method 3, Chemical M, 1.4-bis(alpha-aminobenzyl)benzene is prepared as follows:

Step 1: 1,4-Dibenzoylbenzene is prepared essentially as described by Noelting and Kohn, Ber. 19, 147 (1886). Terephthaloyl dichloride (20.3 g, 0.1 mole) is dissolved in benzene (350 ml) and anhydrous aluminum chloride (30 g, 0.22 mole) is added. The mixture is heated at 70° for 7 hours, cooled to 20° and maintained at this temperature for eighteen hours with continual stirring. The reaction mixture is then added to 1 l crushed ice and 20 ml 37% hydrochloric acid. The benzene solution is washed three times with water and twice with sodium bicarbonate solution. The excess benzene is removed by distillation. The resulting crystalline material is recrystallized from dimethylformamide, yield 22 g (76% of theory) white crystals mp 158°–159°.

Step 2: 1,4-Dibenzoylbenzene dioxime.

The diketone from Step 1 (26 g), hydroxylamine hydrochloride (14g), and sodium acetate (18 g) are refluxed in ethyl alcohol (500 ml) for twenty hours. The precipitate formed on the addition of water (one liter) is filtered, washed with water and dried, yield 28 g (91% of theory) of colorless crystals, mp 230°–233°. [Reported previously by Muenchmeyer, Ber. 19, 1847 (1886)].

Step 3: 1,4-Bis(alpha-aminobenzyl)benzene (M).

The dioxime from Step 2 (30 g) is dissolved in ethyl alcohol (300 ml), saturated with ammonia gas and Raney nickel catalyst W-6 (2 g) added. The mixture is subjected to 700 psi hydrogen pressure and heated at 70° for 3 hours. The catalyst is removed by filtration and 220 ml of ethanol is removed by distillation. The pale yellow precipitate is filtered and dried. Yield 28 g (91% of theory) mp 123°–127°. Calculated for $C_{20}H_{20}N_2$: C, 83.29%; H, 6.99%; N, 9.71%. Found: C, 83.07%; H, 6.89%; N, 9.59%.

EXAMPLE 15

Using Method 3, Chemical N, 1,3-bis(alpha-aminobenzyl) benzene, is prepared from isophthaloyl dichloride and benzene; its structure is confirmed by infrared analysis.

EXAMPLE 16

Using Method 3, Chemical 0, 1,4-bis(4-methoxy-alpha-aminobenzyl)benzene, is prepared from terephthaloyl dichloride and anisole; its structure is confirmed by infrared analysis.

EXAMPLE 17

1,3-Bis(4-methoxy-alpha-aminobenzyl)benzene, Chemical P, is prepared from isophthaloyl dichloride and anisole according to Method 3. Mp of the diamine dihydrochloride is 212°–218°; its structure is confirmed by infrared analysis.

EXAMPLE 18

Terephthaloyl dichloride and phenoxybenzene are used to prepare 1,4-bis(4-phenoxy-alpha-aminobenzyl)-benzene, Chemical Q, by method 3. Structure is confirmed by infrared analysis.

EXAMPLE 19

Method 3 is used to prepare Chemical S, 2,6-bis(4-methyl-alpha-aminobenzyl)pyridine, from 2,6-pyridinedicarboxylic acid dichloride and toluene, and its structure is confirmed by infrared analysis.

EXAMPLE 20

Method 3 is used to prepare Chemical T, 2,5-bis(4-methyl-alpha-aminobenzyl)pyridine, from 2,5-pyridinedicarboxylic acid dichloride and toluene, and its structure is confirmed by infrared analysis.

EXAMPLE 21

This Example illustrates the effectiveness of the presently employed chemicals as bactericides.

Thirty-five mg (or less, to provide the concentrations indicated in Table I, below) of chemical is dissolved in 5 ml acetone to which 45 ml of a 0.01% aqueous solution of a wetting agent (e.g., isooctylphenylpolyethoxyethanol, Triton X-100) is added. Three ml of this preparation is pipetted into a 50 ml Erlenmeyer flask containing 5 ml nutrient agar and kept liquefied at 48°. The bacterial inoculum (0.25 ml) consisting of a cell suspension of Escherichia coli or Staphylococcus aureus is then added to the nutrient-chemical preparation in each flask. Thus each flask containing a chemical concentration of 225 ppm or less. The nutrient-chemical-bacterial mixture is poured into 2½ inch plastic Petri dishes, allowed to harden and incubated at 30°. Observations for growth are made at 24, 48, 72 and 168 hours. The chemical treatments are compared with an untreated, inoculated control using a bacterial growth evaluation of growth or no growth. The results are exemplified by the 48-hour inspection as shown in Table I. The untreated controls of both bacteria show complete coverage of the agar plate surface with bacterial colonies at the time of the 24-hour reading. The data in TABLE I indicate that these chemicals are effective bactericides against a broad spectrum of bacteria such as the Gram-positive type St. aureus as well as the Gram-negative type E. coli.

TABLE I

Bacterial Growth Evaluation; Lowest Serial Dilution Effective to Produce No Growth After 48 Hours Incubation

| Chemical | Dilution (ppm) St. aureus | E. Coli |
|---|---|---|
| A | 64 | 64 |
| B | 8 | 32 |
| C | 255 | N |
| D | 8 | 32 |
| E | 16 | 64 |
| F | 128 | I |
| G | 128 | I |
| H | 64 | 128 |
| I | 128 | N |
| J | 255 | N |
| K | 8 | 64 |
| L | N | 64 |
| M | 128 | 255 |
| N | 128 | 128 |
| O | 128 | 255 |
| P | 128 | 128 |
| Q | 32 | 32 |
| R | N | 8 |
| S | N | 128 |
| T | N | 128 |

N means not tested
I means ineffective at 255 ppm

EXAMPLE 22

This Example illustrates the effectiveness of the presently employed chemicals as bactericides for water-flood operations in secondary oil recovery. The chemicals are tested against anaerobic bacterium Desulfovibrio desulfuricans, a deteriorative agent in secondary oil recovery procedures, fuel storage tanks, pipelines, etc. This test is conducted according to the American Petroleum Institute "Recommended Practice for Biological Analysis of Water-Flood Injection Waters", API-Rp 38, First Edition, May 1959, Section II. In the test, weighted portions of the compounds are dissolved in 10 ml acetone and transferred to 90 ml distilled water containing three drops per liter of a nonionic surface-active agent (isoctylphenylpolyethoxyethanol). Aliquots are removed from this stock solution (usually containing 1,000 or 100 ppm chemical) to sterile, screw-capped, clear one-ounce bottles sufficient to obtain a final concentration of 1, 5, 10, 50 and 100 ppm.

To each bottle is added sulfate reducing broth inoculated with Desulfovibrio desulfuricans (1.5%). The recipe for the sulfate reducing broth is as follows:

| | |
|---|---|
| Sodium lactate, U.S.P. | 4.0 ml |
| Yeast extract | 1.0 g |
| Ascorbic acid | 0.1 g |
| $MgSO_4 \cdot NH_2O$ | 0.2 g |
| $K_2HPO_4$ | 0.01 g |
| $Fe(SO_4)_2(NH_4)_2 \cdot 6H_2O$ | 0.1 g |
| sodium chloride | 10.1 g |
| Distilled water | 1000.0 ml |
| pH adjusted to 7.5 | |

The caps are replaced and the bottles incubated at 32°–35° with daily observations for one week and weekly observations thereafter for a total of 4 weeks incubation. An untreated control without added chemical shows heavy growth after 48 hours incubation. The results of the tests at the 48 hours observations are shown in TABLE II.

TABLE II

Water-flood Operation Evaluation lowest Concentration Effective Against Desulfovibrio desulfuricans

| Chemical | Concentration (ppm) |
|---|---|
| A | 10 |
| B | 5 |
| C | 50 |
| D | 5 |
| E | 5 |
| F | 50 |
| G | 5 |
| H | 50 |

TABLE II-continued

Water-flood Operation Evaluation lowest Concentration Effective Against Desulfovibrio desulfuricans

| Chemical | Concentration (ppm) |
|---|---|
| I | 50 |
| J | 50 |
| K | 50 |
| O | 50 |
| P | 50 |
| Q | 5 |

EXAMPLE 23

This Example evaluates the chemicals of this invention as foliage protectant fungicides using the fungus *Alternaria solani* as the test organism. One gram of the chemical to be tested is ground with 3 ml acetone and 50 mg non-ionic surface active agent (isoctylphenylpolyethoxyethanol). The acetone and surface-active agent are known to be inactive in the biological test run. The mixture is diluted with water, giving suspensions containing 500 to 2000 ppm of the chemical. These suspensions are sprayed on duplicate 6-inch tomato plants (variety Clark's Early Special) using a gun-type sprayer which delivers 2.5 ml per second. The plants are then placed in the greenhouse, together with untreated check plants. Twenty-four hours later the treated and untreated check plants are inoculated with a suspension of *Alternaria solani* spores by means of a 20-second spray from an atomizer sprayer (delivery rate 1 ml per second). The plants are then kept overnight in a control chamber at a temperature of 23.9° and 100% relative humidity. In the morning the plants are transferred to the greenhouse. Three days later the disease is scored by comparing the number of disease lesions of the treated plants with the untreated check.

The formula to determine percent control is:

$$100 - \left( \frac{\text{avg. no. lesions on treated plant}}{\text{avg. no. lesions on untreated plant}} \times 100 \right) = \text{percent control}$$

The results are shown in TABLE III.

TABLE III

Foliage Protectant Fungicidal Spray Evaluation Against Tomato Early Blight (Alternaria solani)

| Chemical | % Disease Control 2000 ppm | 900 ppm |
|---|---|---|
| A | 92 | 82 |
| B | 98 | 95 |
| C | 88 | 78 |
| D | 75 | 72 |
| E | 73 | 76 |
| F | 94 | 81 |
| G | 92 | 85 |
| I | 96 | 66 |
| J | 97 | 96 |
| K | 86 | 91 |
| L | 95 | 90 |
| M | 76 | 84 |
| N | 59 | 87 |
| O | 85 | 65 |
| Q | 97 | 89 |
| R | 75 | 0 |
| S | 85 | 69 |
| T | 95 | 85 |

EXAMPLE 24

This Example evaluates the chemicals of this invention as antimicrobial agents for the preservation of petroleum hydrocarbons. The test is conducted essentially as outlined in "Proposed Procedures for the Screening of Microbial Inhibitors in Hydrocarbon/Water Systems", Society for Industrial Microbiology Special Publication Number 2, pages 3-4.

Ten ml sterile Bushnell-Haas solution is dispensed in sterile 25 × 150 mm screw cap test tubes. An overlay of 10 ml jet fuel (JP-4), sterile, is added to give a 1.1 ratio of hydrocarbon to Bushnell-Haas solution. The test compound is added to the hydrocarbon or water phase depending on the solubility of the test chemical, at concentrations from 100 to 1,000 ppm. The test organisms are added to the tubes in 0.1 ml amounts (*Pseudomonas aeruginosa* and *Cladosporium resinae*). The test tubes are incubated at 25° for 14-28 days with daily agitation and observations for growth. Weekly streak plates are made on Tryptone-glucose extract (TGE) agar and Sabouraud dextrose agar for confirmation of growth. The test media formulations are as follows:

Test Media Formulations

| | Gram/liter Distilled H$_2$O |
|---|---|
| 1. Bushnell-Haas Medium (pH 6.8-7.0) | |
| MgSO$_4$ . PH$_2$O | 0.20 |
| Calcium chloride | 0.02 |
| Potassium phosphate, monobasic | 1.00 |
| Ammonium nitrate | 1.00 |
| Potassium phosphate, dibasic | 1.00 |
| Ferric chloride, 60% aqueous sol. | 2 drops |
| 2. TGE agar (pH 6.8-7.0) | |
| Beef extract | 3.0 |
| Tryptone | 5.0 |
| Glucose | 1.0 |
| Agar | 15.0 |
| 3. Sabouraud Dextrose Agar(ph 5.6) | |
| Peptone | 10.0 |
| Dextrose | 4.0 |
| Agar | 15.0 |

The results, as shown in TABLE IV, are recorded as no growth (O), trace of growth (T), or growth (+).

TABLE IV

Preservation of Petroleum Hydrocarbons Against Bacteria and Fungi; 3-Week Growth Evaluation in Jet Fuel

| | Bacteria | | | Fungi | | |
|---|---|---|---|---|---|---|
| conc. (ppm): | 1000 | 500 | 100 | 1000 | 500 | 100 |
| Chem. | | | | | | |
| A | 0 | 0 | 0 | 0 | 0 | 0 |
| B | 0 | T | + | 0 | 0 | + |
| D | 0 | T | T | 0 | 0 | + |
| E | 0 | 0 | 0 | 0 | 0 | + |

EXAMPLE 25

This Example evaluates Chemical A of the invention against certain pathogenic organisms using a serial dilution method. The chemical is dissolved in acetone and dilutions made in nutrient broths in test tubes. The tubes are inoculated with known amounts of organism suspensions and incubated for 48-96 hours at temperatures optimum for growth (35° for bacteria; 29° for fungi). Observations are made for inhibition of growth, with the results set forth in TABLE V.

TABLE V

| Test Organism | Inhibiting Concentration (ppm) Chemical A |
|---|---|
| Candida albicans | 500 |
| Streptococcus pyogenes | 10 |

TABLE V-continued

| Test Organism | Inhibiting Concentration (ppm) Chemical A |
|---|---|
| Trichophyton mentagrophytes | 20 |

We claim:

1. A chemical containing two diphenylaminomethane groups, linked together by a moiety other than oxygen, having the following formula I:

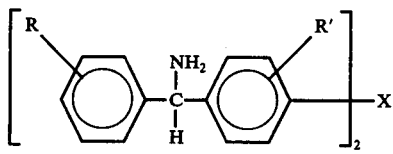

wherein X is furyl fused to one phenyl group of each diphenylaminomethane moiety, and R and R' are the same or different and are selected from the group consisting of hydrogen, methyl, methoxy, and phenoxy.

2. A chemical which is 1,4-bis(4-phenoxy-alpha-aminobenzyl)benzene.

3. A chemical which is 2,5-bis(4-methyl-alpha-aminobenzyl)pyridine.

4. A chemical which is 2,8-bis(alpha-amino-3-methylbenzyl)dibenzofuran.

5. A chemical which is 2,6-bis(4-methyl-alpha-aminobenzyl)pyridine.

6. A composition for the control of bacteria or fungi comprising a chemical containing two dephenylaminomethane groups, linked together by a moiety other than oxygen, having the following formula I, in bactericidally or fungicidally effective amount, and a carrier therefor, said formula being as follows:

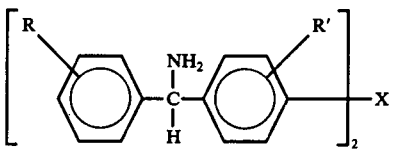

wherein X is furyl fused to one phenyl group of each diphenylaminomethane moiety, and R and R' are the same or different and are selected from the group consisting of hydrogen, methyl, methoxy, and phenoxy.

7. A composition for the control of bacteria or fungi, comprising 1,4-bis(4-phenoxy-alpha-aminobenzyl)benzene, in bactericidally or fungicidally effective amount, and a carrier therefor.

8. A composition for the control of bacteria or fungi comprising 2,5-bis(4-methyl-alpha-aminobenzyl)pyridine, in bactericidally or fungicidally effective amount, and a carrier therefor.

9. A composition for the control of bacteria or fungi comprising 2,8-bis(alpha-amino-3-methylbenzyl)dibenzofuran, in bactericidally or fungicidally effective amount, and a carrier therefor.

10. A composition for the control of bacteria or fungi comprising 2,6-bis(4-methyl-alpha-aminobenzyl)pyridine, in bactericidally or fungicidally effective amount, and a carrier therefor.

* * * * *